(12) United States Patent
Muldoon et al.

(10) Patent No.: US 9,795,569 B2
(45) Date of Patent: *Oct. 24, 2017

(54) PHARMACEUTICAL SOFT GELATIN CAPSULE DOSAGE FORM WITH MODIFIED GUAR GUM

(71) Applicant: Allergan Pharmaceuticals International Limited, Dublin (IE)

(72) Inventors: Brendan Muldoon, Newtownabbey (IE); Ryan Gerald Loughlin, Crumlin (IE); Gerarde Sweeney, Belfast (IE); Emma Karen Boyd, Crumlin (IE)

(73) Assignee: Allergan Pharmaceuticals International Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 14/210,680

(22) Filed: Mar. 14, 2014

(65) Prior Publication Data

US 2014/0271838 A1 Sep. 18, 2014

Related U.S. Application Data

(60) Provisional application No. 61/794,906, filed on Mar. 15, 2013.

(51) Int. Cl.

| A61K 9/48 | (2006.01) |
|---|---|
| A61K 9/66 | (2006.01) |
| A61K 31/565 | (2006.01) |
| A61K 9/00 | (2006.01) |
| A61K 47/10 | (2017.01) |
| A61K 47/22 | (2006.01) |
| A61K 9/06 | (2006.01) |
| A61K 47/36 | (2006.01) |

(52) U.S. Cl.
CPC .......... *A61K 9/4825* (2013.01); *A61K 9/0034* (2013.01); *A61K 9/06* (2013.01); *A61K 9/4866* (2013.01); *A61K 31/565* (2013.01); *A61K 47/10* (2013.01); *A61K 47/22* (2013.01); *A61K 47/36* (2013.01)

(58) Field of Classification Search
CPC ...... A61K 9/48; A61K 9/4808; A61K 9/4816; A61K 9/4825; A61K 9/4833; A61K 9/4841; A61K 9/4858; A61K 9/4875
USPC ................................ 424/451, 452, 456-462
See application file for complete search history.

(56) References Cited

U.S. PATENT DOCUMENTS

| 5,102,666 | A | | 4/1992 | Acharya | |
|---|---|---|---|---|---|
| 5,874,106 | A | | 2/1999 | Adesunloye et al. | |
| 5,919,481 | A | * | 7/1999 | Cody | A61K 9/4866 424/452 |
| 5,989,535 | A | | 11/1999 | Nayak | |
| 6,024,980 | A | * | 2/2000 | Hoy | A61K 9/4808 424/451 |
| 6,060,077 | A | | 5/2000 | Meignant | |
| 6,187,747 | B1 | * | 2/2001 | Singh | A61K 9/4858 424/185.1 |
| 7,067,504 | B2 | | 6/2006 | King et al. | |
| 7,067,505 | B2 | | 6/2006 | King et al. | |
| 7,468,070 | B2 | | 12/2008 | Raina et al. | |
| 7,485,323 | B2 | | 2/2009 | Dolphin et al. | |
| 7,795,241 | B2 | | 9/2010 | Keown et al. | |
| 2004/0131670 | A1 | | 7/2004 | Gao | |
| 2005/0142185 | A1 | * | 6/2005 | Beleno et al. | 424/451 |
| 2006/0110415 | A1 | * | 5/2006 | Gupta | A61K 8/0212 424/401 |
| 2007/0004694 | A1 | | 1/2007 | Woolfson et al. | |
| 2007/0015741 | A1 | | 1/2007 | Keown et al. | |
| 2007/0066837 | A1 | | 3/2007 | Kamal et al. | |
| 2007/0098783 | A1 | * | 5/2007 | Sukuru | A61K 9/4858 424/451 |
| 2007/0104778 | A1 | | 5/2007 | Zeng et al. | |
| 2008/0090569 | A1 | | 4/2008 | Khan et al. | |
| 2008/0122993 | A1 | | 5/2008 | Nakamichi et al. | |
| 2008/0305168 | A1 | | 12/2008 | Moon et al. | |
| 2010/0056493 | A1 | | 3/2010 | Jain et al. | |
| 2011/0003000 | A1 | | 1/2011 | DiPiano et al. | |

FOREIGN PATENT DOCUMENTS

| EP | 0243930 B1 | 4/1987 |
|---|---|---|
| EP | 0770384 A1 | 5/1997 |
| WO | 2007/066837 A1 | 6/2007 |
| WO | 2007/091856 A1 | 8/2007 |
| WO | 2008/090569 A1 | 7/2008 |
| WO | 2008/122993 A1 | 10/2008 |
| WO | 2011018800 A2 | 2/2011 |

OTHER PUBLICATIONS

Carstensen et al., "Pellicule Formation in Gelatin Capsules," Drug Development and Industrial Pharmacy, vol. 19, p. 2709-2712 (1993).
Digenis et al., "Cross-Linking of Gelatin Capsules and Its Relevance to Their in Vitro-In Vivo Performance," Journal of Pharmaceutical Sciences, vol. 83(7), pp. 915-921 (Jul. 1994).
Hakata et al., "Effect of Storage Temperature on the Physicochemical Properties of Soft Galatin Capsule Shells," Chem. Pharrn. Bull. vol. 42(7), pp. 1496-1500 (1994).
Adesunloye et al., "Effect of Glycine/Citric Acid on the Disolution Stability of Hard Gelatin," Drug Development and Industrial Pharmacy, vol. 24(6), pp. 493-500 (1998).
Venugopal et al., "Evaluation of Gelatins for Cross-Linking Potential," Pharmaceutical Technology, Drug Delivery, pp. 32-34, 36 and 37 (2001).
Sinha et al., "Poly saccharides in colon-specific drug delivery," International Journal of Pharmaceutics, vol. 224, pp. 19-38 (2001).
Singh et al., "Alternation of Dissolution Characteristics of Gelatin-Containing Formulations," Pharmaceutical Technology, pp. 36-58 (2002).

(Continued)

*Primary Examiner* — Micah-Paul Young
(74) *Attorney, Agent, or Firm* — Fitzpatrick, Cella, Harper & Scinto

(57) ABSTRACT

A pharmaceutical soft gelatin capsule dosage form that includes (a) a shell that includes gelatin; and (b) a fill that includes at least one active ingredient, one or more polyethylene glycol, and a modified guar gum. The pharmaceutical soft gelatin capsule dosage form maintains its shell integrity (hardness) and fill viscosity after storage.

20 Claims, 9 Drawing Sheets

(56) References Cited

OTHER PUBLICATIONS

Singh et al., "Gelatin-Containing Formulations: Changes in Dissolution Characteristics," Encyclopedia of Pharmaceutical Technology, pp. 195-209 (2003).
G. N. Foulks "Clinical Evaluation of the Efficacy of PEG/PG Lubricant Eye Drops with Gelling Agent (HP-GUAR) for the Relief of the Signs and Symptoms of Dry Eye Disease: A Review," Drugs of Today, vol. 43(12), pp. 887-896 (2007).
Alam et al., "Development and Evaluation of Acid-buffering Bioadhesive Vaginal Tablet for Mixed Vaginal Infections," AAPS PharmSciTech, pp. E1-E8 (2007).
Cole et al., "Challenges and Opportunities in the Encapsulation of Liquid and Semi-Solid Formulations into Capsules for Oral Administration," Advanced Drug Delivery Review, vol. 60, pp. 747-756 (2008).
Azarmi et al., "Current Perspectives in Dissolution Testing of Conventional and Novel Dosage Forms," International Journal of Pharmaceutics, vol. 328, pp. 12-21 (2007).
R. P. Gullapalli, "Soft Gelatin Capsules (Softgels)," Journal of Pharmaceutical Sciences, vol. 99(10), pp. 4107-4148 (2010).
Risica et al., "Rheological Properties of Guar and its Methyl, Hydroxypropyl and Hydroxypropyl-Methyl Derivatives in Semidilute and Concentrated Aqueous Solutions," Polymer, vol. 51, pp. 1972-1982 (2010).
Horn et al., "Soft Gelatin Capsules I: Factors Affecting Capsule Shell Dissolution Rate," Pharmaceutical Technology, vol. 62(6) pp. 1001-1006 (1973).
Product Data Sheet N000753, Jaguar® HP-105, pp. 1-2 (Oct. 2007).
Product Data Sheet N000886, Jaguar® HP-120, pp. 1 (Oct. 2010).
ISR and Written Opinion from PCT Application No. PCT/US2014/027093 dated Jun. 26, 2014.
ISR and Written Opinion from PCT Application No. PCT/US2014/027145 dated Jul. 3, 2014.
Mythri et al., "Novel Mucoadhesive Polymers—A Review, " Journal of Applied Pharmaceutical Science, pp. 37-42, (2011).

* cited by examiner

Fig. 1: Rheological profile of a 90% PEG 400:10% PEG 3350 formulation. Each value is the average of at least 5 replicates (n ≥ 5).
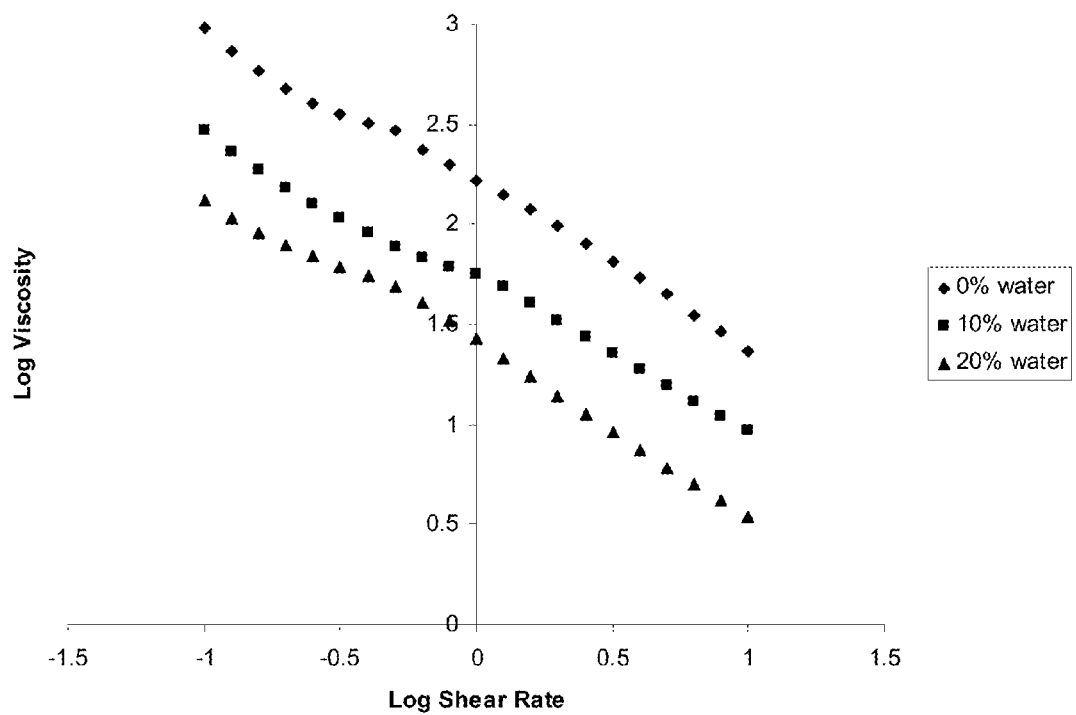

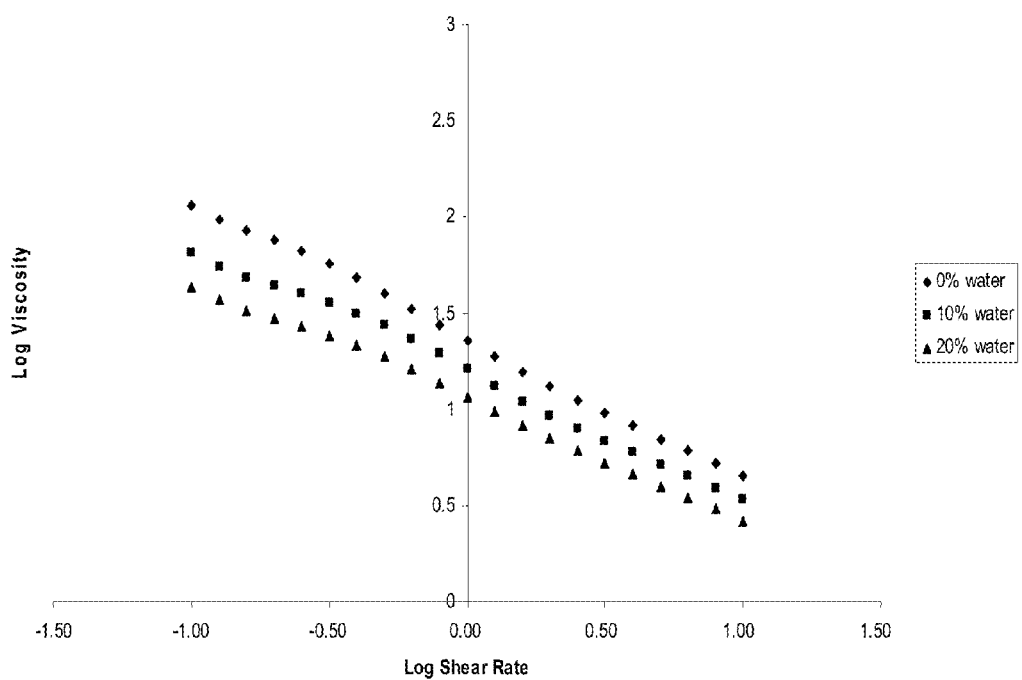
Fig. 2: Rheological profile of a regular guar gum formulation with the addition of 10% and 20% water. Each value is the average of at least 5 replicates (n ≥ 5).

Fig. 3: Rheological profile of a modified guar gum formulation with the addition of 10%, 20% and 30% water. Each value is the average of at least 5 replicates (n ≥ 5).
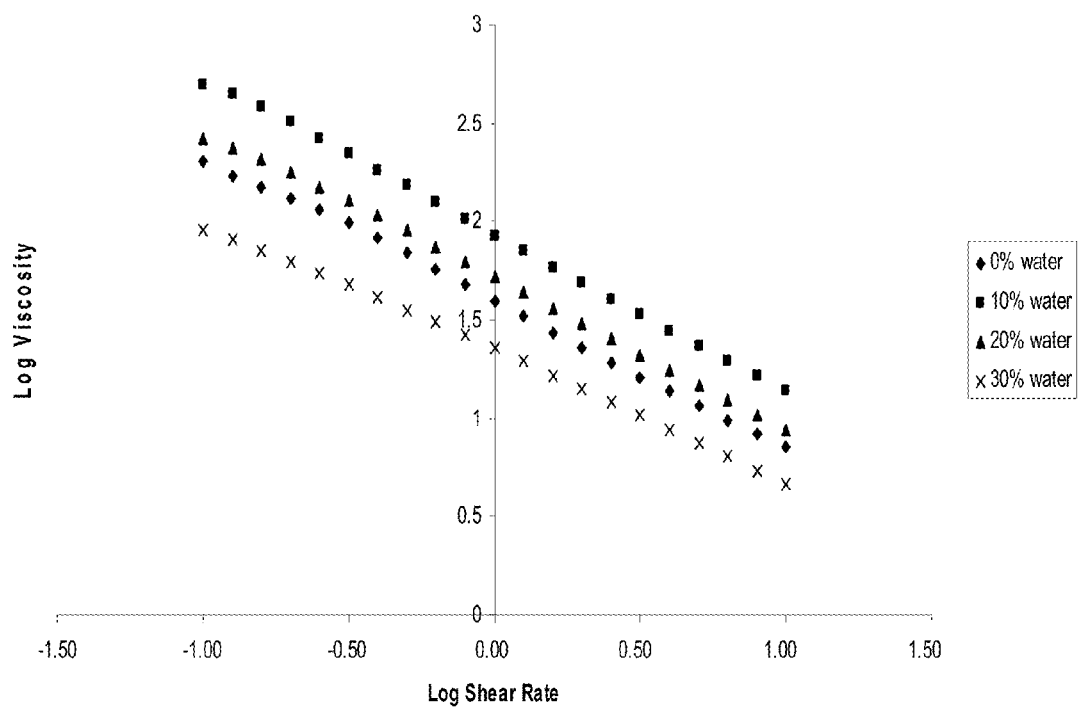

Fig. 4: Effect of water content on the adhesiveness of formulations with and without modified guar gum.
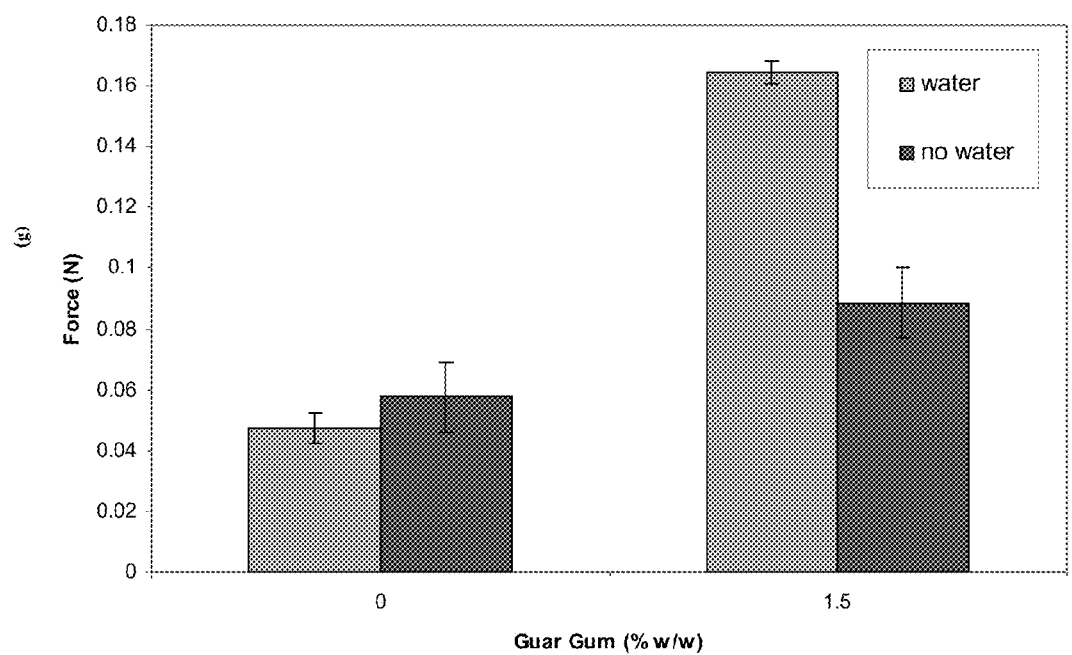

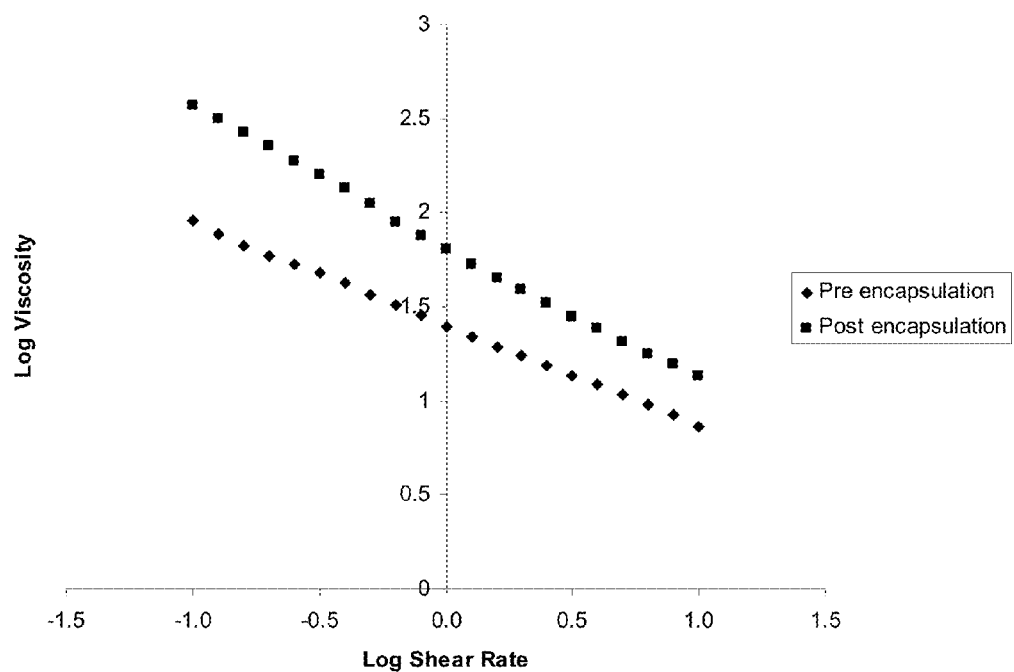
Fig. 5: Rheological profiles pre-encapsulation and post-encapsulation of a modified guar gum/ PEG 400 fill formulation of an embodiment of the present invention.

Fig. 6: Rheological profile of a modified guar gum/ PEG 400 fill formulation of an embodiment of the present invention after storage.
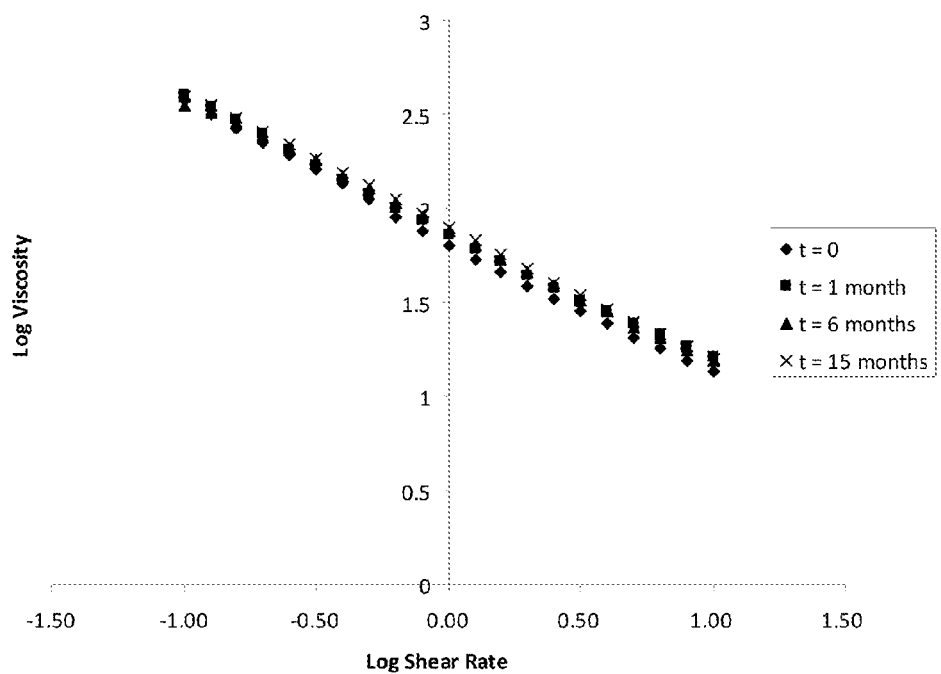

Fig. 7: Effect of storage on the hardness of a pharmaceutical soft gelatin capsule dosage form of an embodiment of the present invention.
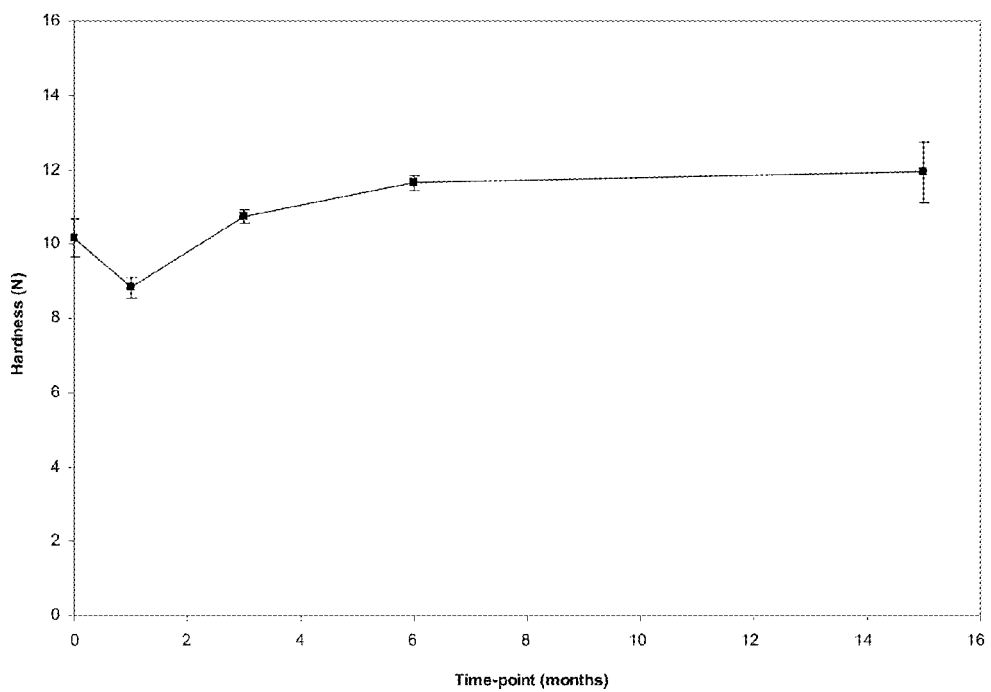

Fig. 8: Dissolution profile of various embodiments of the present invention. Each value is the average of 3 replicates (n = 3).
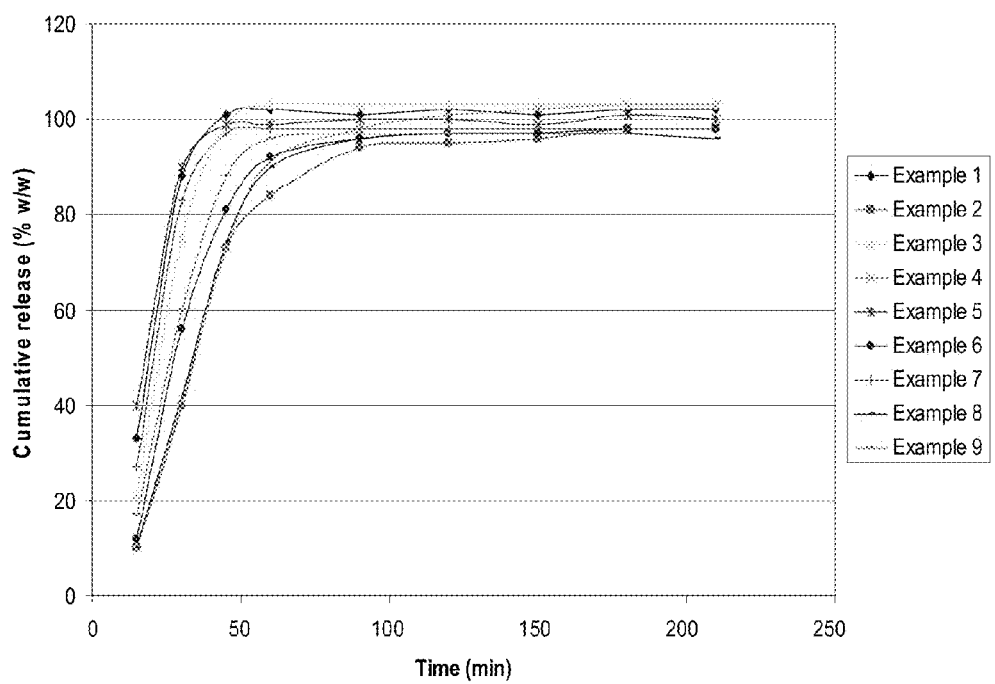

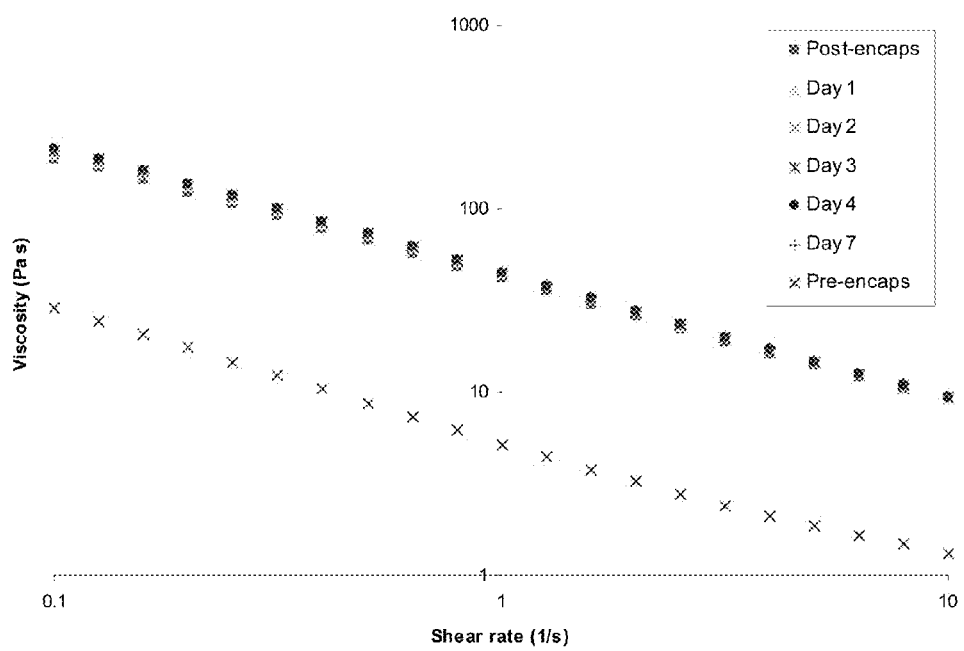
Fig. 9: Rheological profile of a modified guar gum/ PEG 400 fill formulation and the effect of drying at Pre-encapsulation, Post Encapsulation and Days on Drying.

PHARMACEUTICAL SOFT GELATIN CAPSULE DOSAGE FORM WITH MODIFIED GUAR GUM

CROSS-REFERENCE TO RELATED APPLICATION

This application claims the benefit of U.S. Provisional Patent Application No. 61/794,906, filed Mar. 15, 2013, the entire disclosure of which is incorporated by reference herein.

BACKGROUND OF THE INVENTION

Field of the Invention

This invention relates to a pharmaceutical soft gelatin capsule dosage form that may be advantageously used for vaginal administration of a pharmaceutically active ingredient in a muco-adhesively enhanced capsule fill. The soft gelatin capsule dosage form of the invention maintains its shell integrity (hardness) and fill viscosity over the time of storage.

Description of Related Art

Soft gelatin pharmaceutical formulations have several advantages, such as, they are easy to swallow, they mask the odors and unpleasant tastes, and once swallowed, they release their contents very quickly. However, soft gelatin capsules have been known to have a decrease in dissolution during storage, which eventually may retard or deleteriously impact drug release. The decrease in dissolution has typically been attributed to the crosslinking of gelatin in the capsule shell resulting in a pellicle formation. Pellicle formation can be minimized by various techniques such as using excipients in the capsule fill with low grade peroxides and aldehydes, or using gelatin grades less prone to pellicle formation to minimize the formation of crosslinking agents. The manufacturing process can also be optimized, for example, by storing fill under nitrogen, controlling the temperature and humidity of manufacturing environment, minimizing the temperature and heat exposure time of heating processes, testing excipients for formaldehyde or low molecular weight aldehydes levels, and using moisture and/or light resistant packaging.

Applicants have found that even when steps are taken to minimize pellicle formation, soft gelatin capsules containing ionic components such as polyacrylic acid in the fill can exhibit unstable dissolution profiles after storage. It is believed, without being bound by theory, that the polyacrylic acid contained in the fill of the soft gelatin capsule interacts with the gelatin in the shell, inhibiting rupture and thus altering the dissolution profile. Thus, it may be advantageous to provide a soft gelatin capsule dosage form that employs non-ionic components in the fill in order to avoid an unstable dissolution profile after storage.

Vaginal administration of a pharmaceutically active ingredient using a soft gelatin capsule not only requires a stable dissolution profile over storage time, but also requires a fill containing a pharmaceutically active ingredient that maintains a consistent viscosity over time and has muco-adhesive properties that ensure consistent and efficacious application of the active ingredient to the mucosal wall of the vaginal cavity.

Accordingly, it would be advantageous to provide a pharmaceutical soft gelatin capsule dosage form that does not contain ionic components, but which can deliver a low dose drug, such as an estrogen, in a muco-adhesively enhanced fill, while maintaining its shell integrity (hardness) and fill viscosity even after the capsule has been in storage up to one year, preferably 18 months, or more preferably, two years.

SUMMARY OF THE INVENTION

The present invention is directed to a pharmaceutical soft gelatin capsule dosage form comprising: (a) a shell comprising gelatin and a plasticizer; and (b) a fill comprising at least one pharmaceutically active ingredient, one or more polyethylene glycol, and a modified guar gum. The pharmaceutical soft gelatin capsule dosage form maintains its shell integrity (hardness) after storage and includes an advantageous gel matrix fill that maintains its viscosity over storage.

In one embodiment, the pharmaceutical soft gelatin capsule dosage form of the invention is used for vaginal administration. In yet another embodiment, the modified guar gum is hydroxypropyl guar gum.

Another embodiment of the present invention is a pharmaceutical soft gelatin capsule dosage form comprising: (a) a shell comprising gelatin and a plasticizer; and (b) a fill comprising at least one pharmaceutically active ingredient, one or more polyethylene glycol, and a modified guar gum, wherein the fill after encapsulation has a log viscosity of about 1 to about 2 times greater than the log viscosity of the fill before encapsulation over a log shear rate of about −1.0 to about 1.0. In one embodiment, the fill is in the form of a hydrophilic gel and the hydrophilic gel is formed in situ after encapsulation of the fill.

BRIEF DESCRIPTION OF THE DRAWINGS

FIG. 1 is a plot depicting the rheological profile of a 90% PEG 400:10% PEG 3350 formulation with the addition of 10% and 20% water to the fill.

FIG. 2 is a plot depicting the rheological profile of a regular guar gum formulation with the addition of 10% and 20% water to the fill.

FIG. 3 is a plot depicting the rheological profile of a modified guar gum formulation with the addition of 10%, 20% and 30% water to the fill.

FIG. 4 is a plot depicting the effect of water content on the adhesiveness of formulations with and without modified guar gum. Each value is the average±standard deviation of at least 5 replicates (n≥5).

FIG. 5 is a plot depicting the rheological profiles of a fill pre-encapsulation and post-encapsulation for the soft gelatin capsule dosage form of an embodiment of the present invention. Each value is the average of at least 5 replicates (n≥5).

FIG. 6 is a plot depicting the rheological profile of a modified guar gum/PEG 400 fill formulation of an embodiment of the present invention after storage at t=0, t=1 month, t=6 months and t=15 months. Each value is the average of at least 5 replicates (n≥5).

FIG. 7 is a plot depicting the effect of storage on the hardness of a pharmaceutical soft gelatin capsule dosage form of an embodiment of the present invention with a modified guar gum/PEG 400 fill formulation. Each value is the average±standard deviation of at least 5 replicates (n≥5) and the coefficient of variation is less than 7%.

FIG. 8 is a dissolution profile of various embodiments of the present invention.

FIG. 9 is a plot depicting the rheological profile and the effect of drying on an embodiment of the invention at pre-encapsulation, post-encapsulation and daily throughout the drying process. Each value is the average of 3 replicates (n=3).

DETAILED DESCRIPTION OF THE INVENTION

An embodiment of the present invention is directed to a pharmaceutical soft gelatin capsule dosage form comprising: (a) a shell comprising gelatin and a plasticizer; and (b) a fill comprising at least one pharmaceutically active ingredient, one or more polyethylene glycol, and a modified guar gum.

The pharmaceutical soft gelatin capsule dosage form of the invention may be administered orally or vaginally, but provides particularly advantageous properties when used vaginally. A particular embodiment includes the pharmaceutical soft gelatin capsule dosage form wherein the pharmaceutically active ingredient is estrogen and which is administered vaginally.

As used herein "pharmaceutically acceptable" means the component is appropriate for oral or vaginal administration to humans. In one embodiment, the component must be considered appropriate for application to the vaginal environment.

Soft gelatin capsules are well known and are often described as softgels. They comprise a one-piece, hermetically sealed gelatin-based shell containing a solution, a suspension, or a semisolid which is referred to as the fill formulation, fill material or fill. The gelatin Bloom strength in the soft gelatin capsule is typically about 150 to about 200 Bloom (or grams). Exemplary manufacturers of softgels include Catalent Pharma Solutions, Somerset, N.J., Pharmagel Engineering spa, Lodi, Italy, and Soft Gel Technologies Inc., Commerce, Calif. The soft gelatin capsule of the invention is a pharmaceutical dosage form that comprises a gelatin-based shell and a fill.

In an embodiment of the present invention, the shell may comprise gelatin and a plasticizer. The shell may optionally include an opacifier and/or dyes. Gelatin is obtained by the partial hydrolysis of collagen derived from the skin, white connective tissue and bones of animals including cattle, pigs and fish. It mainly consists of water soluble proteins (84-90% w/w) along with mineral salts (1-2% w/w) and water (8-15% w/w). The protein fraction contains amino acids linked by amide bonds in a polypeptide chain.

Collagen is a fibrous protein and the main constituent of animal skin, bone and connective tissue. It consists of a triple helix of three polypeptide chains with a molecular weight of approximately 300,000 Da. Denaturation involves breaking of the hydrogen bonds to destabilize the collagen helix resulting in a marked decrease in the molecular weight and the intrinsic viscosity. Hydrolysis of collagen by boiling bones or skins in water results in a low yield of impure gelatin with poor physical properties. Therefore, commercial manufacture of gelatin involves initial removal of contaminants before thermal denaturing with the aid of either a dilute acid to result in Type A gelatin or a dilute alkali to result in Type B gelatin. Gelatin is amphoteric in nature with its isoelectric points ranging from 6.0 to 9.0 for Type A gelatin and from 4.7 to 5.3 for Type B gelatin. It is believed that the alkaline hydrolysis causes a greater degree of deamidation of the asparagine and glutamine amino acids in collagen, resulting in a larger number of free carboxylic acid compared to acid hydrolysis. Examples of suitable Type A gelatin include without limitation acid bone gelatin. Examples of suitable Type B gelatin include without limitation lime bone gelatin.

The gelatin-based soft gelatin capsule will generally contain water in an amount of about 1% to about 25%, more preferably about 1% to about 15%, still more preferably about 5% to about 10% by weight of the gelatin shell after the fill has been encapsulated and water has migrated from the capsule to the fill. Without being bound by theory, it is believed that the water in the gelatin capsule, e.g., 20% to 50% by weight, prior to filling, migrates at least in part to assist with gelling the fill and increasing its viscosity.

In a preferred embodiment, gelatin is present in an amount of about 35% to about 85%, more preferably about 40% to about 80% by weight of the gelatin shell.

In an embodiment of the present invention, any pharmaceutically acceptable plasticizer can be used. Non-limiting examples of suitable plasticizer include polyhydric alcohols such as sorbitol, glycerin, mannitol, xylitol, and sorbitan; dialkylphthalates; lower alkyl citrates wherein the lower alkyl has 1-6 carbon atoms; glycols and polyglycols including polyethylene glycols with a molecular weight range of about 200 to about 2,000, methoxyl-propylene-glycol, and 1,2-propylene glycol; esters of polyhydroxy-alcohols such as mono-, di-, and tri-acetate of glycerol; ricinoleic acid and esters thereof; and mixtures of the above.

In a preferred embodiment, plasticizer is present in an amount of about 10% to about 60%, more preferably about 20% to about 55%, still more preferably about 30% to about 50% by weight of the gelatin shell.

In an embodiment of the present invention, the fill includes at least one pharmaceutically active ingredient, one or more polyethylene glycol, and a modified guar gum. The fill does not contain ingredients in an amount that would not be pharmaceutically acceptable for oral or vaginal administration.

Non-limiting examples of suitable pharmaceutically active ingredient include steroids and low dose non-steroidal compounds, their pharmaceutically acceptable salts, esters, hydrates, prodrugs and derivatives. Non-limiting examples of suitable low dose non-steroidal compounds include darifenacin, udenafil and bisphosphonate compounds like risedronate, alendronate, etidronate, ibandronate, clodronate, and zoledronate. Preferably, the active ingredient is an estrogenic or progestogenic compound such as, estradiol, ethinyl estradiol, estetrol, norethindrone acetate, etonogestrel, their pharmaceutically acceptable salts, esters, hydrates, prodrugs and derivatives, and mixtures thereof.

The phrase "pharmaceutically acceptable salt" of a compound as used herein means a salt that is pharmaceutically acceptable and that possesses the desired pharmacological activity of the parent compound. Pharmaceutically acceptable salts include salts of acidic or basic groups present in a compound of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Suitable base salts include, but are not limited to, aluminum, calcium, lithium, magnesium, potassium, sodium, zinc, and diethanolamine salts.

The term "ester", as used herein, refers to an organic compound made by replacing the hydrogen of an acid by an alkyl, e.g., $C_1$ to $C_6$ alkyl, or other organic group. Various esters are well known in the art. Nonlimiting examples of esters include formate, acetate, propionate, acetyl glycolate and butyrate.

The term "hydrate", as used herein, refers to a compound formed by the addition of water. The hydrates may be obtained by any known method in the art by dissolving the compounds in water and recrystallizing them to incorporate water into the crystalline structure. Nonlimiting examples of hydrates include hemihydrate, monohydrate, dehydrate, trihydrate, and pentahydrate.

The term "prodrug", as used herein, refers to an inactive precursor of a drug, converted into its active form in the body by normal metabolic processes. Various forms of prodrugs are well known in the art.

In one embodiment, the pharmaceutically active ingredient is present in the soft gelatin capsule of the present invention in an amount of about 0.01 µg to about 500 mg, depending on the desired dosage of the active ingredient.

In an embodiment, when the pharmaceutically active ingredient is estrogen, it is included in the pharmaceutical soft gelatin capsule dosage form of the present invention in an amount ranging from about 0.00001% to about 2%, more preferably from about 0.00015% to about 0.0075%, still more preferably about 0.003% by weight of the pharmaceutical capsule fill.

In an embodiment, the at least one active ingredient is estrogen. In a preferred embodiment, the estrogen is 17β-estradiol, mestranol, conjugated estrogens USP, estrone, estetrol, or ethinyl estradiol or salts, esters or prodrugs thereof. Other suitable estrogens include those described in each of U.S. Pat. Nos. 7,067,504, 7,067,505, and 7,795,241, and U.S. Patent Application Publication Nos. 2007/0015741 and 2007/0004694. The disclosures of each of these patents and patent application publications are incorporated in their entirety by reference herein.

In a preferred embodiment, the at least one active ingredient is selected from the group consisting of estradiol, its salts, esters, hydrates, prodrugs and its derivatives. In a preferred embodiment, estrogen is 17β-estradiol. Pharmaceutically acceptable salt of 17β-estradiol are well known and include, without limitation, 17β-estradiol hydrochloride salt, β-estradiol 17-(β-D-glucuronide) sodium salt and β-estradiol 3-(β-D-glucuronide) 17-sulfate dipotassium salt. Esters of 17β-estradiol are also well known and include, without limitation, estradiol-3-acetate, estradiol-17-acetate, estradiol-3,17-diacetate, estradiol-3,17-valerate, estradiol-3-valerate, estradiol-17-valerate, estradiol 3-benzoate, estradiol cypionate, estradiol dipropionate, and estradiol enantate. Hydrates of 17β-estradiol are also well known and include, without limitation, the hemihydrate. Prodrugs of 17β-estradiol are also well known and include, without limitation, the prodrug described in U.S. Pat. No. 7,067,505. In a preferred embodiment, the 17β-estradiol is 17β-estradiol hemihydrate. In another preferred embodiment, the active ingredient is estetrol.

The phrase "modified guar gum" as used herein means guar gum which is chemically modified by using reactive functional groups to substitute free hydroxyl groups along the macromolecular backbone. A modified guar gum used in this invention includes a mixture of modified guar gums. Preferably, the modified guar gum is hydroxypropyl guar gum (e.g., commercially available under the tradename Jaguar® HP120 (Rhodia)). Preferably the level of substitution is above about 0.6, more preferably about 1.0 to about 1.5 and most preferably about 1.2. In an embodiment of the present invention, the modified guar gum is present in the fill in an amount of about 0.5% to about 3.0%, more preferably about 0.5% to about 1.5% by weight of the total weight of the fill. It was found that addition of polyethylene glycol, such as PEG 3350, helped to address the elasticity problems, including the problems discussed in Examples below at lower levels of modified guar gum.

The fill comprises one or more polyethylene glycol. In an embodiment of the present invention, the polyethylene glycol has a molecular weight range of about 200 to about 900. In a preferred embodiment, the polyethylene glycol has a molecular weight less than 900. In an embodiment of the present invention, the fill comprises at least one additional polyethylene glycol with a molecular weight of greater than 900. In an embodiment of the present invention, the fill comprises two polyethylene glycols, with the second polyethylene glycol having a molecular weight of greater than 900, and the weight ratio of the first and the second polyethylene glycols ranges from about 99:1 to about 1:99. In a preferred embodiment, the PEG 400 and PEG 3350 are present in a weight ratio ranging from 60:40 to 95:5, more preferably, the PEG 400:PEG 3350 weight ratio ranges from 90:10 to 95:5.

In an embodiment of the present invention, the fill may optionally contain solvent. Non-limiting examples of suitable solvents include propylene glycol, acetone, ethanol, butylene glycol, diethylene glycol monoethyl ether, dipropylene glycol, glycerin, polyethyelene glycol, mineral oil, peanut oil, sesame oil. In a preferred embodiment, the solvent is propylene glycol. In an embodiment of the present invention, solvent is present in the fill in an amount of about 1% to 20%, more preferably about 5% to about 15%, still more preferably about 5% by weight of the total weight of the fill.

In an embodiment of the present invention, the fill also comprises an antioxidant. Non-limiting examples of suitable antioxidant include tocopherol, butylated hydroxytoluene, butylated hydroxyanisole, dodecyl gallate, octyl gallate, propyl gallate, ascorbyl palmitate, sodium ascorbate and thymol. In a preferred embodiment, the antioxidant is tocopherol.

The inventors of the present invention found a decrease in the dissolution of soft gelatin capsules during storage that contained ionic components such as polyacrylic acid. However, the various known techniques described above to minimize pellicle formation did not help alleviate the problem. The inventors then concluded that the decrease in dissolution was not caused by pellicle formation and hypothesized that it could be caused by the interaction of gelatin with the anionic polymer in the fill.

As previously noted, while not wishing to be bound by theory, it was discovered that because polyacrylic acid such as polycarbophil in the fill is an anionic polymer, it interacted with the gelatin to result in the formation of an insoluble mass, which reduces the dissolution stability of the soft gelatin capsule dosage form. Other anionic polymers in the fill besides polyacrylic acid also interact with gelatin to result in the formation of an insoluble mass. Non-limiting examples of such anionic polymers include poly(methyl vinyl ether/maleic anhydride) (Gantrez)#, carbomer, carboxymethylcellulose calcium, carboxymethylcellulose sodium and alginates, such as calcium alginate, potassium alginate, sodium alginate, and alginic acid.

Various polymers were investigated as a suitable alternate to polyacrylic acids, such as polycarbophil, in the fill. Rheological analysis of the fill formulation was conducted to investigate the flow properties, in particular, to determine the viscosity and how this varied following storage at 25°

C./60% RH. In an embodiment of the present invention, the pharmaceutical soft gelatin capsule dosage form is substantially free of polyacrylic acid, it can deliver a low dose drug, such as an estrogen, and maintain its hardness and fill viscosity even after the capsule has been in storage up to one, or more preferably, two years. As used herein, substantially free means no polyacrylic acid or an amount that does not cause dissolution instability, e.g., less than 1% percent by weight of the fill.

Viscosity is an important quality attribute of the softgel fill as it can have a significant impact on the in vivo retention and thus the clinical benefit of the finished softgel product. Viscosity of the fill formulation of the samples set forth and tested in the Examples below was measured by performing continuous flow rheology at 25° C. using a cone and plate rheometer. The contents of 2 size 20 oval softgels or equivalent amount of pre-encapsulated fill were tested for each replicate. Samples were applied to the lower plate of the rheometer and allowed to equilibrate for 5 minutes prior to testing. The shear rate was increased from 0.1 to 10 $s^{-1}$ with 10 samples per decade. In an embodiment of the present invention, the viscosity of the fill measured as described above at zero log shear rate will range from about 1 to about 5 log viscosity after encapsulation.

Softgel capsule shell integrity (hardness) is another critical quality attribute as the samples must maintain suitable hardness to ensure that they can be handled and administered appropriately by the patient. Hardness of the samples set forth and tested in the Examples below was measured using a Bareiss hardness tester. The instrument operates by compressing the softgel between a plunger attached to a load cell and a platform which is automatically raised. The softgel is placed horizontally on the platform with its seam contour aligned parallel to the platform. The platform rises automatically and the load cell indicator displays the value of the resistance of the softgel to the compressive force. This value is displayed in Newtons (N) and represents the hardness of the softgel under test.

Specific embodiments of the invention will now be demonstrated by reference to the following examples. It should be understood that these examples are disclosed by way of illustrating the invention and should not be taken in any way to limit the scope of the present invention.

EXAMPLES

In order to identify an alternate polymer to anionic polymers, such as polycarbophil, and assess its suitability for incorporation into hydrophilic fill formulations, various polymers were investigated. The polymers studied included hypromellose, carrageenan, regular guar gum, hydroxypropyl guar gum and hydroxyethyl cellulose (HEC). Viscosity of the fill formulation was measured by performing continuous flow rheology as described above. A formulation containing polycarbophil was initially prepared to provide a visual comparison for the gels manufactured with an alternate polymer. The fill was a clear homogenous gel which flowed under gravity. The addition of hypromellose instead of the polycarbophil did not result in a homogenous gel being formed but rather as a consolidated mass throughout the fill. The carrageenan and HEC did not form gels at the levels investigated. On the other hand, the modified guar gum (e.g., hydroxypropyl guar gum) formed a viscous gel which dramatically increased in viscosity with increasing levels of the polymer. The formulations containing 2% and 3% hydroxypropyl guar gum were very viscous compared to the polycarbophil gel so lower levels of 1.5% and 1.75% hydroxypropyl guar gum were also studied. These lower levels improved the flow properties of the gel, however, it was noted that the formulations were very elastic which could present issues with encapsulation and effective seal formation.

The effect of polyethylene glycol on viscosity of the fill was studied in formulations containing PEG 400 and PEG 3350. Various ratios of PEG 400:PEG 3350 were studied ranging from 60:40 to 90:10. It was found that increasing the PEG 400 content reduced the viscosity of the formulation and the formulation with a 90:10 ratio was able to flow under gravity. It was also found that challenging these systems with increasing levels of water resulted in a loss of viscosity as shown in the rheological profile in FIG. 1 for a 90% PEG 400:10% PEG 3350 formulation and in the viscosity data at zero log shear rate in Table 1. 10%, 20% and 30% w/w water was added to the fill at 60° C. before the mixtures were cooled to room temperature. The addition of 30% w/w water to the fill resulted in a complete loss of viscosity with sedimentation and could not be tested on the rheometer.

TABLE 1

| % Water | Viscosity (Pa s) | Log Viscosity |
| --- | --- | --- |
| 0 | 156.15 | 2.22 |
| 10 | 56.72 | 1.75 |
| 20 | 26.7 | 1.43 |

A range of hydrophilic polymers were then incorporated into the formulation (90% PEG 400:10% PEG 3350) with the aim of allowing the formulation to resist the changes in viscosity. These included HEC, hydroxypropyl cellulose (HPC), regular guar gum and a modified guar gum. The HEC, HPC and regular guar gum did not maintain the viscosity of the formulation as shown in the example rheological profile in FIG. 2 when compared to the data in FIG. 1, whereby there is a statistically significant (p<0.5) reduction in the viscosity with increased water levels. The viscosity data at zero log shear rate for regular guar gum formulation is shown in Table 2.

TABLE 2

| % Water | Viscosity (Pa s) | Log Viscosity |
| --- | --- | --- |
| 0 | 22.57 | 1.35 |
| 10 | 16.14 | 1.21 |
| 20 | 11.55 | 1.06 |

Replacing the regular guar gum with the hydroxypropyl guar gum resulted in a formulation that could maintain its viscosity on the addition of 10% and 20% w/w water to the fill as shown in FIG. 3 when compared to the data in FIG. 1. The formulation also remained intact with the addition of 30% water to the fill unlike the other samples with no sedimentation occurring. The hydroxypropyl guar gum enabled faster hydration resulting in the formulation gelling on addition of water rather than being diluted. The viscosity data at zero log shear rate for hydroxypropyl guar gum formulation is shown in Table 3.

TABLE 3

| % Water | Viscosity (Pa s) | Log Viscosity |
|---|---|---|
| 0 | 39.56 | 1.60 |
| 10 | 85.47 | 1.93 |
| 20 | 52.25 | 1.72 |
| 30 | 22.63 | 1.36 |

The effect of modified guar gum on the muco-adhesiveness of the formulations with and without the addition of water was studied by measuring the force required to remove a hydrated mucin disk from the surface of the fill. Approximately 15 g of material was placed in a glass beaker and the force required to remove a pre-hydrated mucin disc from the surface of the sample was measured using a TA.XTplus texture analyser. The mucin disc consisted of 2 g of mucin and Avicel PH105 in a 1:1 ratio, compressed using 25 mm flat faced tooling at a compression force of 7 tonnes using a single station press. The disc was pre-hydrated with a 5% w/w mucin solution, blotted to remove excess solution and attached to the probe on the load cell of the texture analyser. The probe was manually lowered to ensure even contact with the test material. After 30 seconds, the test was initiated, with the probe lifting the disc out of the sample at a speed of 0 5 mm/s and the maximum force on the resultant force–distance curve recorded. Three replicates were performed for each sample, with fresh discs and fresh sample tested each time. The fill material was tested before and after the addition of 6% w/w water to simulate moisture ingress from the capsule shell material and induce gelation.

The results presented in FIG. 4 show that the inclusion of modified guar gum results in a marked increase in the adhesiveness of the sample. They also demonstrate the significant increase in adhesiveness following gelation of the fill material.

An exemplary fill formulation according to the present invention that was studied is set forth in Table 4.

TABLE 4

| Component | Function | Quantity (% w/w) |
|---|---|---|
| Estradiol USP | Active ingredient | 0.003 |
| Propylene glycol USP | Solvent | 5.00 |
| Polyethylene glycol 400 NF | Vehicle | 83.9 |
| Modified guar gum (Jaguar ® HP120) | Gelling agent | 1.50 |
| Tocopherol | Antioxidant | 0.6 |
| Polyethylene glycol 3350 NF | Viscosity modifier | 9.00 |

The physical stability of pharmaceutical soft gelatin capsule dosage form according to an embodiment of the present invention containing a PEG/modified guar gum fill formulation was studied. The pharmaceutical soft gelatin capsule dosage form with fill and shell compositions as set forth in Table 5 and Table 6, respectively, was packaged into ACLAR® blisters with foil lidding.

TABLE 5

| Component | Quantity (mg/capsule) | Quantity (% w/w) | Quantity (g/batch) |
|---|---|---|---|
| Estradiol USP | 0.01 | 0.00083 | 0.033 |
| Propylene glycol USP | 60.0 | 5.00 | 200 |
| PEG 400 NF | 1014.0 | 84.5 | 3380 |
| Modified guar gum (Jaguar ® HP120) | 18.0 | 1.50 | 60.0 |
| PEG 3350 NF | 108.0 | 9.00 | 360 |
| TOTAL | 1200.0 | 100.0 | 4000 |

TABLE 6

| Component | Quantity (mg/dry capsule) | Quantity (% w/w) | Quantity (Kg/batch) |
|---|---|---|---|
| Gelatin NF (Type A 200 bloom) | 222.2 | 40.0 | 4.0 |
| Sorbitol Special Blend (50/50 Glycerin) | 166.6 | 30.0 | 3.0 |
| Purified Water USP | N/A | 30.0 | 3.0 |
| TOTAL | 388.8 | 100.0 | 10.0 |

The effect of encapsulation on the viscosity of the modified guar gum/PEG 400 fill formulation is displayed in FIG. 5. The results demonstrate a significant increase in the viscosity of the fill post-encapsulation. The fill after encapsulation is in the form of a hydrophilic gel and has a log viscosity of about 1 to about 2 times greater than the log viscosity of the fill before encapsulation over a log shear rate of about −1.0 to about 1.0. This is due to hydration of the modified guar gum/PEG 400 fill by water transferred from the capsule shell and results in the formation of a viscous gel material. The water level in the fill material prior to encapsulation is typically less than 1.0% w/w, increasing to approximately 6.0 to 11.0% w/w following encapsulation. This highly viscous fill would be very difficult to encapsulate using standard softgel manufacturing techniques and thus the ability of the gel to form in situ after encapsulation overcomes this difficulty and therefore provides a significant advantage. The viscosity data at zero log shear rate for the pre and post encapsulated fill is shown in Table 7.

TABLE 7

| Fill Material | Viscosity (Pa s) | Log Viscosity |
|---|---|---|
| Pre encapsulation | 24.77 | 1.39 |
| Post encapsulation | 63.66 | 1.80 |

The above pharmaceutical soft gelatin capsule dosage form packaged into ACLAR® blisters with foil lidding was stored on stability at 25° C./60%RH for 15 months. The hardness and fill viscosity of the softgels were tested initially and at t=1, 3, 6 and 15 months. The hardness of the softgel was measured using a Bareiss hardness tester as described above. The viscosity of the fill was measured by performing continuous flow rheology as described above.

The effect of storage on the viscosity of the modified guar gum/PEG 400 fill formulation is displayed in FIG. 6. These results demonstrate that these systems maintain their viscosity following 15 months stability storage at 25° C./60% RH.

The effect of storage on the hardness of the softgels is presented in FIG. 7. These results indicate that the softgels maintain their hardness following 15 months stability storage at 25° C./60% RH, i.e there is no apparent reduction in hardness that would detrimentally affect the ability of the patient to handle and administer the dosage form.

As seen from the results in FIG. 6 and FIG. 7, pharmaceutical soft gelatin capsule dosage forms containing a modified guar gum/PEG 400 fill formulation are physically stable following 15 months stability storage at 25° C./60% RH.

The dissolution properties of pharmaceutical soft gelatin capsule dosage forms according to an embodiment of the present invention containing a PEG/modified guar gum fill formulation were studied. 500 mg of the fill formulation was encapsulated in gel material consisting of acid bone gelatin and sorbitol special/glycerin blend A810, which is a blend of 1,4-sorbitan, sorbitol and mannitol (sorbitol sorbitan solution NF) and glycerin USP. Water is used in the manufacture of the gel material up to approximately 40% by weight of wet gel mass solution, however, by the end of the capsule manufacturing process, which involved a number of drying steps, capsules typically have approximately 2% to 15% water by weight of soft gelatin capsule. Eight different fills were selected for this investigation. The compositions of the fill formulations according to various embodiments of the present invention that were studied are set forth in Table 8.

TABLE 8

| | Quantity (% w/w) | | | | | | | |
|---|---|---|---|---|---|---|---|---|
| Component | Example 1 | Example 2 | Example 3 | Example 4 | Example 5 | Example 6 | Example 7 | Example 8 |
| Estradiol USP | 0.003 | 0.003 | 0.003 | 0.003 | 0.003 | 0.003 | 0.003 | 0.003 |
| PEG 400 | 88.3 | 87.3 | 85.3 | 84.3 | 87.5 | 86.5 | 84.5 | 83.5 |
| Propylene glycol | 5.0 | 5 | 5 | 5 | 5 | 5 | 5 | 5 |
| Modified Guar Gum (Jaguar ® HP120) | 0.5 | 1.5 | 0.5 | 1.5 | 0.5 | 1.5 | 0.5 | 1.5 |
| PEG 3350 | 6 | 6 | 9 | 9 | 6 | 6 | 9 | 9 |
| Tocopherol | 0.2 | 0.2 | 0.2 | 0.2 | 1 | 1 | 1 | 1 |
| Total | 100.0 | 100.0 | 100.0 | 100.0 | 100.0 | 100.0 | 100.0 | 100.0 |

The dissolution of the pharmaceutical soft gelatin capsule dosage form was measured by the following dissolution method. The dissolution was measured using a USP Apparatus 2 with paddles as the dissolution apparatus, a dissolution medium volume of 500 ml of pH 4.5 acetate buffer, a paddle speed of 50 rpm and a temperature of 37±0.5° C. The dissolution profiles are displayed in FIG. 8. These results demonstrate a pharmaceutically acceptable drug release profile for the fill formulations described in the present invention.

The effect of drying on the fill viscosity is presented in FIG. 9. The fill formulation detailed in Table 9 was manufactured and tested for viscosity prior to encapsulation, post-encapsulation and daily throughout the drying process. Capsules were spread evenly on trays and placed in a drying cabinet. The capsules were dried under moderate drying conditions at a temperature of 21-24° C. and a relative humidity of 20-30%. These results demonstrate that the increased viscosity is achieved once the fill is encapsulated and is maintained throughout the drying process.

TABLE 9

| Component | Quantity (mg/capsule) | Quantity (% w/w) | Quantity (kg/batch) |
|---|---|---|---|
| Estradiol USP | 0.015 | 0.003 | 0.003 |
| Propylene glycol USP | 25.00 | 5.00 | 5.5 |
| PEG 400 NF | 429.5 | 85.9 | 94.49 |
| Modified guar gum (Jaguar ® HP120) | 5.00 | 1.00 | 1.10 |
| PEG 3350 NF | 37.5 | 7.50 | 8.25 |
| DL-α-tocopherol | 3.00 | 0.60 | 0.66 |
| TOTAL | 500.0 | 100.0 | 110.0 |

The following Points are non-limiting embodiments of the present invention:

Point 1. A pharmaceutical soft gelatin capsule dosage form comprising:
    a shell comprising gelatin and a plasticizer; and
    a fill comprising at least one pharmaceutically active ingredient, one or more polyethylene glycol, and a modified guar gum.

Point 2. The pharmaceutical soft gelatin capsule dosage form of Point 1, wherein the modified guar gum is present in an amount of about 0.5% to about 3.0% by weight of the fill.

Point 3. The pharmaceutical soft gelatin capsule dosage form of Point 2, wherein the modified guar gum has a level of substitution above 0.6.

Point 4. The pharmaceutical soft gelatin capsule dosage form of Point 3, wherein the modified guar gum has a level of substitution from about 1.0 to about 1.5.

Point 5. The pharmaceutical soft gelatin capsule dosage form of Point 4, wherein the modified guar gum has a level of substitution of about 1.2.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A pharmaceutical soft gelatin capsule dosage form comprising:
a shell comprising gelatin and a plasticizer; and
a fill encapsulated by the shell, the fill containing less than 1.0% w/w water prior to encapsulation and further comprising at least one pharmaceutically active ingredient, one or more polyethylene glycol, and a modified guar gum; and wherein the fill after encapsulation has a log viscosity of about 1 to about 2 times greater than the log viscosity of the fill before encapsulation over a log shear rate of about −1.0 to about 1.0.

2. The pharmaceutical soft gelatin capsule dosage form of claim 1, wherein the pharmaceutical soft gelatin capsule dosage form is for oral or vaginal administration.

3. The pharmaceutical soft gelatin capsule dosage form of claim 2, wherein the pharmaceutical soft gelatin capsule dosage form is for vaginal administration.

4. The pharmaceutical soft gelatin capsule dosage form of claim 2, wherein the at least one active ingredient is selected from the group consisting of steroids and low dose non-steroidal compounds, their pharmaceutically acceptable salts, esters, hydrates, prodrugs and derivatives.

5. The pharmaceutical soft gelatin capsule dosage form of claim 4, wherein the at least one active ingredient is selected from the group consisting of estradiol, ethinyl estradiol, norethindrone acetate, etonogestrel, darifenacin, udenafil, risedronate, alendronate, etidronate, ibandronate, clodronate, and zoledronate.

6. The pharmaceutical soft gelatin capsule dosage form of claim 4, wherein the at least one active ingredient is selected from the group consisting of estradiol, its salts, esters, hydrates, prodrugs and its derivatives.

7. The pharmaceutical soft gelatin capsule dosage form of claim 6, wherein the amount of the modified guar gum is about 0.5% to about 3.0% by weight of the fill.

8. The pharmaceutical soft gelatin capsule dosage form of claim 7, wherein the modified guar gum is hydroxypropyl guar gum.

9. The pharmaceutical soft gelatin capsule dosage form of claim 1, wherein the polyethylene glycol has a molecular weight of less than 900.

10. The pharmaceutical soft gelatin capsule dosage form of claim 9 further comprising at least one additional polyethylene glycol with a molecular weight of greater than 900.

11. The pharmaceutical soft gelatin capsule dosage form of claim 10, wherein the polyethylene glycol is a combination of PEG 400 and PEG 3350.

12. The pharmaceutical soft gelatin capsule dosage form of claim 11, wherein the PEG 400 and PEG 3350 are present in weight ratio of between 90:10 and 95:5.

13. The pharmaceutical soft gelatin capsule dosage form of claim 1, wherein the fill further comprises an antioxidant.

14. The pharmaceutical soft gelatin capsule dosage form of claim 13, wherein the antioxidant is tocopherol.

15. The pharmaceutical soft gelatin capsule dosage form of claim 1, wherein the fill further comprises a solvent.

16. The pharmaceutical soft gelatin capsule dosage form of claim 15, wherein the solvent is propylene glycol.

17. The pharmaceutical soft gelatin capsule dosage form of claim 16, wherein the propylene glycol is present in an amount of about 5% by weight of the total weight of the fill.

18. The pharmaceutical soft gelatin capsule dosage form of claim 8, wherein the hydroxypropyl guar gum is about 1.5% by weight of the fill.

19. A pharmaceutical soft gelatin capsule dosage form comprising:
a shell comprising gelatin and a plasticizer; and
a fill comprising at least one pharmaceutically active ingredient, one or more polyethylene glycol, and a modified guar gum,
wherein the fill after encapsulation has a log viscosity of about 1 to about 2 times greater than the log viscosity of the fill before encapsulation over a log shear rate of about −1.0 to about 1.0; and wherein the fill has less than 1.0% w/w of water prior to encapsulation and about 6.0 to 10.0% w/w of water after encapsulation.

20. The pharmaceutical soft gelatin capsule dosage form of claim 1, wherein the modified guar gum is about 0.5% to about 3.0% by weight of the fill.

* * * * *